US009610035B2

(12) United States Patent
Aarts et al.

(10) Patent No.: US 9,610,035 B2
(45) Date of Patent: Apr. 4, 2017

(54) METHOD AND SYSTEM FOR MAINTAINING A STATE IN A SUBJECT (75) Inventors: Ronaldus Maria Aarts, Eindhoven (NL); Mark Thomas Johnson, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 297 days.

(21) Appl. No.: 12/920,876

(22) PCT Filed: Mar. 5, 2009

(86) PCT No.: PCT/IB2009/050905
§ 371 (c)(1),
(2), (4) Date: Sep. 3, 2010

(87) PCT Pub. No.: WO2009/112983
PCT Pub. Date: Sep. 17, 2009

(65) Prior Publication Data
US 2011/0015468 A1    Jan. 20, 2011

(30) Foreign Application Priority Data
Mar. 14, 2008    (EP) .................................... 08152729

(51) Int. Cl.
*A61M 21/00*    (2006.01)
*A61B 5/18*    (2006.01)
(Continued)

(52) U.S. Cl.
CPC .............. *A61B 5/18* (2013.01); *A61B 5/0205* (2013.01); *A61B 5/0245* (2013.01);
(Continued)

(58) Field of Classification Search
CPC . A61B 5/0205; A61B 5/02405; A61B 5/0245; A61B 5/165; A61B 5/18;
(Continued)

(56) References Cited

U.S. PATENT DOCUMENTS 4,569,536 A * 2/1986 Tsuge et al. .................. 280/807
5,902,250 A * 5/1999 Verrier et al. ................ 600/515
(Continued)

FOREIGN PATENT DOCUMENTS

DE    102005035850 A1    2/2007
EP        0978256 A1    2/2000
(Continued)

OTHER PUBLICATIONS

Moore, S.: "Calm in Your Palm; Biofeedback Device Promises to Reduce Stress"; IEEE Spectrum; Mar. 2006; www.spectrum.ieee.org.; p. 1.
(Continued)

*Primary Examiner* — Christine H Matthews (57) ABSTRACT

A method of maintaining a state in a subject includes measuring one or more physiological parameters of the subject, calculating, using the measured parameter(s), a value, determining if the calculated value is below a lower threshold or above an upper threshold, and generating an output to the subject if the calculated value is determined to be below the lower threshold or above the upper threshold. In one embodiment, the generating an output to the subject includes generating a first output if the calculated value is determined to be below the lower threshold and generating a second output if the calculated value is determined to be above the upper threshold, the second output being different from the first output.

16 Claims, 6 Drawing Sheets

(51) Int. Cl.
*A61B 5/0205* (2006.01)
*A61B 5/024* (2006.01)
*A61B 5/0245* (2006.01)
*A61B 5/0456* (2006.01)
*A61B 5/16* (2006.01)
*A61B 5/00* (2006.01)

(52) U.S. Cl.
CPC ........ *A61B 5/02405* (2013.01); *A61B 5/0456* (2013.01); *A61B 5/165* (2013.01); *A61B 5/486* (2013.01); *A61M 21/00* (2013.01); *A61M 2021/0022* (2013.01); *A61M 2021/0055* (2013.01); *A61M 2021/0066* (2013.01); *A61M 2021/0083* (2013.01); *A61M 2230/06* (2013.01); *A61M 2230/42* (2013.01)

(58) Field of Classification Search
CPC .......... A61B 5/486; A61M 2021/0083; A61M 21/00; A61M 2230/06; A61M 2230/42; A61M 21/02; A61M 2021/0011
USPC .................. 600/26–28, 509; 340/500, 573.1; 180/271–272; 701/1
See application file for complete search history.

(56) References Cited

U.S. PATENT DOCUMENTS

| | | | |
|---|---|---|---|
| 6,097,295 | A | 8/2000 | Griesinger et al. |
| 6,212,135 | B1 | 4/2001 | Schreiber |
| 6,305,943 | B1 | 10/2001 | Pougatchev et al. |
| 6,358,201 | B1 | 3/2002 | Childre et al. |
| 6,398,745 | B1* | 6/2002 | Sherman et al. ............... 601/41 |
| 6,720,743 | B2* | 4/2004 | Yano et al. .................... 315/291 |
| 7,117,032 | B2 | 10/2006 | Childre et al. |
| 7,163,512 | B1 | 1/2007 | Childre et al. |
| 7,616,125 | B2* | 11/2009 | Johns ............................ 340/576 |
| 2003/0100924 | A1 | 5/2003 | Foreman et al. |
| 2003/0144572 | A1 | 7/2003 | Oschman et al. |
| 2003/0146841 | A1 | 8/2003 | Koenig |
| 2003/0149344 | A1* | 8/2003 | Nizan ........................... 600/300 |
| 2004/0225340 | A1 | 11/2004 | Evans |
| 2004/0243013 | A1* | 12/2004 | Kawachi et al. ............. 600/509 |
| 2005/0033189 | A1 | 2/2005 | McCraty et al. |
| 2005/0124906 | A1 | 6/2005 | Childre et al. |
| 2005/0256419 | A1 | 11/2005 | Roach et al. |
| 2005/0288601 | A1 | 12/2005 | Wood et al. |
| 2006/0047202 | A1 | 3/2006 | Elliott |
| 2006/0058590 | A1 | 3/2006 | Shaw et al. |
| 2006/0111745 | A1 | 5/2006 | Foreman et al. |
| 2006/0111746 | A1 | 5/2006 | Foreman et al. |
| 2007/0007067 | A1 | 1/2007 | Pollehn et al. |
| 2007/0021675 | A1 | 1/2007 | Childre et al. |
| 2007/0156031 | A1* | 7/2007 | Sullivan et al. .............. 600/300 |
| 2007/0182529 | A1 | 8/2007 | Dobler et al. |
| 2008/0119994 | A1* | 5/2008 | Kameyama ..................... 701/48 |
| 2009/0030263 | A1* | 1/2009 | Heruth et al. ................... 600/26 |
| 2010/0130808 | A1* | 5/2010 | Hattori ............................. 600/9 |

FOREIGN PATENT DOCUMENTS

| | | |
|---|---|---|
| EP | 1393679 A1 | 3/2004 |
| GB | 2315332 A | 1/1998 |
| JP | 2003245357 A | 9/2003 |
| JP | 20050890970 A | 3/2005 |
| JP | 2005237456 A | 9/2005 |
| JP | 2007512989 A | 5/2007 |
| WO | 2007072288 A1 | 6/2007 |
| WO | 2007136338 A1 | 11/2007 |

OTHER PUBLICATIONS

Rzeczinski et al: "Regions of Cardiorespiratory Synchronization in Humans Under Paced Respiration"; Physical Review E, vol. 66, 2002, pp. 051909-1-051909-9.
International Search Report; PCT/IB2009050905. International Filing Date May 3, 2009.
"Awake-System for Effective Assessment of Driver Vigilance and Warning According to Traffic Risk Estimation"; European Project IST-2000-28062, European Commission on Information Society Technologies, Balocco, Italy, Sep. 2004, Downloaded at http://www.awake-eu.org/objectives.html on Sep. 17, 2010.
Cysarz et al: "Cardiorespiratory Synchronization During Zen Meditation"; European Journal of Applied Physiology, vol. 95, 2005, pp. 88-95.
Jovanov, E.: "On Spectral Analysis of Heart Rate Variability During Very Slow Yogic Breathing"; Proceedings of the 2005 IEEE 27th Annual Conference on Engineering in Medicine and Biology, Shanghai, China, Sep. 2005, pp. 2467-2470.
Junnila et al: "An EMFi-Film Sensor Based Ballistocardiographic Chair: Performance and Cycle Extraction Method"; IEEE Workshop on Signal Processing Systems Design and Implementation, 2005, Issue 2-4, pp. 373-377.
Harland et al: "High Resolution Ambulatory Electrocardiographic Monitoring Using Wrist-Mounted Electric Potential Sensors"; Measurement Science and Technology, vol. 14, 2003, pp. 923-928.
Brink et al: "Contact-Free Measurement of Heart Rate, Respiration Rate, and Body Movements During Sleep"; Behavior Research Methods, vol. 38, 2006, pp. 511-521.
Morbiducci et al: "Optical Vibrocardiography: A Novel Tool for the Optical Monitoring of Cardiac Activity"; Annals of Biomedical Engineering, vol. 35, No. 1, Jan. 2007, pp. 45-58.
Patterson et al: "Voluntary Cardio-Respiratory Synchronization"; IEEE Engineering in Medicine and Biology Magazine, Nov./Dec. 2004, pp. 52-56.
Han et al, "Decomposition of Heart Rate Variability by Adaptive Filtering for Estimation of Cardiac Vagal Tone", IEEE Engineering in Medicine and Biology Society, vol. 13, No. 2, 1991, pp. 660-661, XP000348278.
Shin, "Assessment of Autonomic Regulation of Heart Rate Variability by the Method of Complex Demodulation", IEEE Transactions on Biomedical Engineering, vol. 36, No. 2, 1989, p. 274-283, XP000009587.
Nilsson, "Respiratory Monitoring Using Reflection Mode Photoplethysmography", PhD Thesis No. 898, 2005, p. 1-2.
Berntson et al, "Heart Rate Variability: Origins, Methods, and Interpretive Caveats", Physchophsiology, vol. 34, 1997, p. 623-648.
Zhao et al, "Derivation of Respiration From Electrocardiogram Druing Heart Rate Variability Studies", Computers in Cardiology, XP-002322495, 1994, p. 53-56.
Task Force of the European Society of Cardiology the North American Society of Pacing Electrophysiology, Special Report, "Heart Rate Variability Standards of Measurement, Physiological Interpretation and Clinical Use", 1996, p. 1043-1065.

* cited by examiner

METHOD AND SYSTEM FOR MAINTAINING A STATE IN A SUBJECT

FIELD OF THE INVENTION

This invention relates to a method of and system for maintaining a state in a subject. In one embodiment the invention provides an emotion control system with upper and lower thresholds.

BACKGROUND OF THE INVENTION

It is known to monitor physiological parameters of subjects in medical and safety environments. Whilst several products are available which aim to continuously increase the level of relaxation of the user (for example, RESPeR-ATE®, StressEraser) there are many situations (such as operating dangerous machinery) where it could be dangerous to be too relaxed as this could result in the user falling asleep, or moving towards a dangerously low level of alertness. This (hypo-vigilance) is a known issue and there are approaches to prevent this happening (see for example the project "AWAKE", European project IST-2000-28062, http://www.awake-eu.org/objectives.html) However, in still more circumstances in general situations where people are interacting not just with machinery but also with other people (for example when driving, at work, aircraft pilots, train drivers, shop assistants or counter workers in banks, local council, call centre personnel etc.), it is important not only to stay alert (i.e. to limit the amount of relaxation, as described above) but also to avoid becoming too stressed or too aroused, as this will also limit the ability of the individual to function optimally.

The system referred to above as "RESPeRATE®" (see for example the website http://www.resperate.com/) is a portable electronic device that helps a subject lower their blood pressure and stress levels naturally by device-guided breathing. The device uses the body's natural tendency to follow external rhythms interactively guiding the user to reduce their breathing rate to a "therapeutic zone" of less than 10 breaths per minute. This system is the only medical device clinically proven to lower blood pressure through paced breathing therapy and is available for sale without a prescription (over-the-counter—OTC). Another product which operates to reduce stress in patients is the StressEraser (see for example United States Patent Application Publication US 2005/0288601). Both of these products aim to continuously reduce stress levels and as such provide no facility to limit the lower level of stress—indeed when using both products it may be pleasant for the user to fall asleep.

However, in certain cases (such as operating dangerous machinery) it is not desirable for a subject to fall asleep: it could be dangerous to be too relaxed as this could result in the user falling asleep. This is known from the European project "AWAKE" mentioned above. One purpose of this project is to provide a system that prevents a vehicle driver from falling asleep. In such a case of hypo-vigilance the system will provide an adequate warning to the driver with various levels of warnings, according to the estimated driver's hypo-vigilance state and also to the actual traffic environment. This system will operate reliably and effectively in all highway scenarios.

A similar system known as the "Driver Warning System" also referred to as "DWS" can use acoustic, visual and haptic means according to the type of AWAKE warning. Acoustic warnings include different warning tones to raise the driver's alertness and speech messages to indicate why the warning has been activated. Visual elements of the alarm are either located at the rear view mirror for the demo cars or at an external box on top of the dashboard of the truck demonstrator. These devices also host a smart card reader and the On/Off button of the system. The haptic warning is based on a vibration device attached to the seat belt lock. The vibrations stimulus can be felt all along the seat belt.

There does not exist, however, a system that can monitor the state of a subject and respond to the subject in order to maintain a specific state in the subject, without that subject becoming either too aroused or too relaxed.

SUMMARY OF THE INVENTION

It is therefore an object of the invention to improve upon the known art.

According to a first aspect of the present invention there is provided a method of maintaining a state in a subject comprising: measuring one or more physiological parameters of the subject, calculating, using the measured parameter(s), a value, determining if the calculated value is below a lower threshold or above an upper threshold, and generating an output to the subject if the calculated value is determined to be below the lower threshold or above the upper threshold.

According to a second aspect of the present invention there is provided a system for maintaining a state in a subject comprising: one or more sensors arranged to measure one or more physiological parameters of the subject, a processor arranged to calculate, using the measured parameter(s), a value, and to determine if the calculated value is below a lower threshold or above an upper threshold, and one or more output devices arranged to generate an output to the subject if the calculated value is determined to be below the lower threshold or above the upper threshold.

Owing to the invention it is possible to provide a system that monitors the subject and provides an indication to the subject if they are deemed to have deviated sufficiently from a desired state whether that is because the subject has become too aroused or too relaxed. The system and method is provided to assist users in situations such as driving to remain in a region of affective state (e.g. relaxation or arousal) defined by both a lower threshold and an upper threshold. Whilst many of the examples in this document will be presented in terms of the relaxation state of a user whilst in a driving situation it is clear that the invention can be advantageously applied in many other situations (as listed above with reference to the prior art) and for many other affective stares (such as fear, anger, surprise, boredom, disgust, happiness etc.).

In one embodiment the output device(s) is/are arranged to generate a first output if the calculated value is determined to be below the lower threshold and to generate a second output if the calculated value is determined to be above the upper threshold the second output being different from the first output. The system can provide appropriate stimuli if the subject is becoming too tired and likewise if the subject is becoming too alert or stressed then a different stimuli can be used.

Preferably the processor is arranged to map the one or more measured physiological parameters of the subject to a scale and wherein the calculated value comprises a value on the scale. If the system is configured to measure a single parameter of the subject such as the subject's heart rate then the value calculated will be a direct physical measurement and the two thresholds could be 80 BPM as the lower threshold and 130 BPM as the upper threshold. The system is configured to provide an output to the subject whenever the measured heart rate is outside this range.

However, if multiple physiological parameters are being measured such as heart rate, skin conductivity, and head movement, then these physical measurements can be mapped to a scale (such as a relaxation scale) which is effectively an interpretation of the underlying physical data. This state scale could be a simple scale running from 1 to 10, where the mapping function takes all the measured data and provides a value that is then placed on this scale. The thresholds used to determine whether an output is to be provided to the subject are levels on this scale. This allows more flexibility in the decision making process for whether to provide an output to the subject. For example heart rate may be used to determine the upper levels in the scale whereby a faster heart rate indicates that the subject is becoming stressed. However, if the measured heart rate is below 100 BPM for example this may (according to the mapping function) have no more input into the perceived scale and head movement or facial expression may be used to calculate the lower levels of the scale.

It is furthermore possible that one threshold may be described in terms of a first mapped parameter, e.g. relaxation, whilst the other threshold is described by a second mapped parameter, e.g. anger. Clearly it is furthermore possible that measurements of different physiological parameters or sets of parameters may be required to derive the different mapped parameters.

Preferably an output device is arranged to provide direct physical feedback to the subject. In many embodiments it is desirable to provide direct physical feedback to the subject's body in order to stimulate a rapid response from the subject. For example in the system provided to ensure that a driver remains alert but not stressed an output device can comprise a belt for engaging the subject's body and a tightening device arranged to control the tightness of the belt. This can be used to regulate the breathing of the subject using the tightening and the slackening of the seat belt under the control of the tightening device to regulate the in and out action of the subject's breathing. In the in-vehicle embodiment an output device may comprise a portion of a seat for the subject also including the seat safety features such as the seat belt and/or an output device may comprise a portion of a steering wheel for the subject. These output device(s) can be arranged to output a vibration or alternatively a heat pulse. Other possible in-vehicle solutions include an output device that comprises an air conditioning system and a control device arranged to control the air conditioning system. The air conditioning system could be used to generate repeated cues to promote guided breathing such as producing repeated gusts of air and/or repeated scent releases.

BRIEF DESCRIPTION OF THE DRAWINGS

Embodiments of the present invention will now be described by way of example only with reference to the accompanying drawings in which:—

DETAILED DESCRIPTION OF THE EMBODIMENTS

Figure 1:
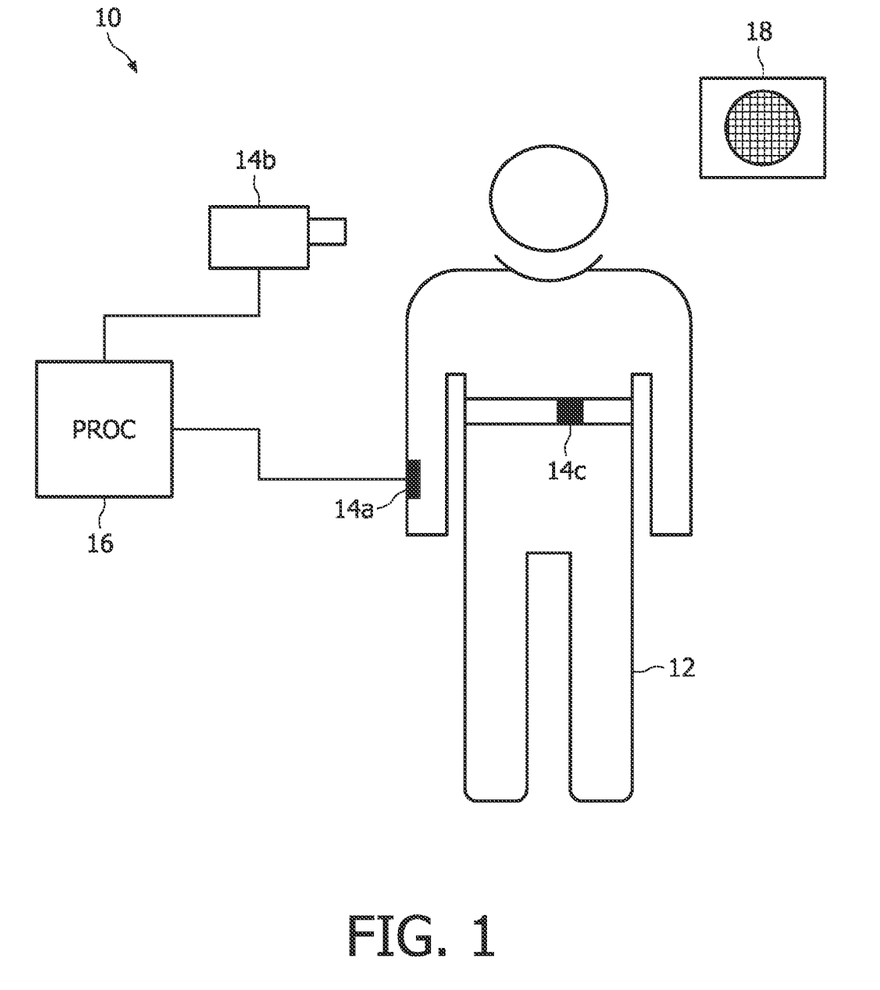
FIG. 1 is a schematic diagram of a system with a subject.

FIG. 1 shows a system 10 for maintaining a state in a subject 12. The system 10 comprises sensors 14 which are arranged to measure one or more physiological parameters of the subject 12 a processor 16 arranged to calculate using the measured parameter(s), a value and to determine if the calculated value is below a lower threshold or above an upper threshold and an output device 18 arranged to generate an output to the subject 12 if the calculated value is determined to be below the lower threshold or above the upper threshold. The Fig. shows the subject 12 being monitored by three separate sensors 14. The sensor 14a is skin conductivity measuring device, the sensor 14b is a camera that is monitoring the facial expression and head position of the subject 12, and the sensor 14c is a wireless heart rate monitor held in place with a strap around the subject's chest. The sensors 14a and 14c can be considered to be direct sensors that are directly measuring physiological parameters of the subject 12, and the sensor 14b is an indirect sensor that is measuring physiological parameters such as the facial expression of the subject 12. Other indirect physiological sensors may comprise the manner in which user interacts with a user interface, for example the pressure at which the user grips a steering wheel. The output device 18 is a loudspeaker arranged to output audio instructions to the subject 18 under the control of the processor 16.

Figure 2:
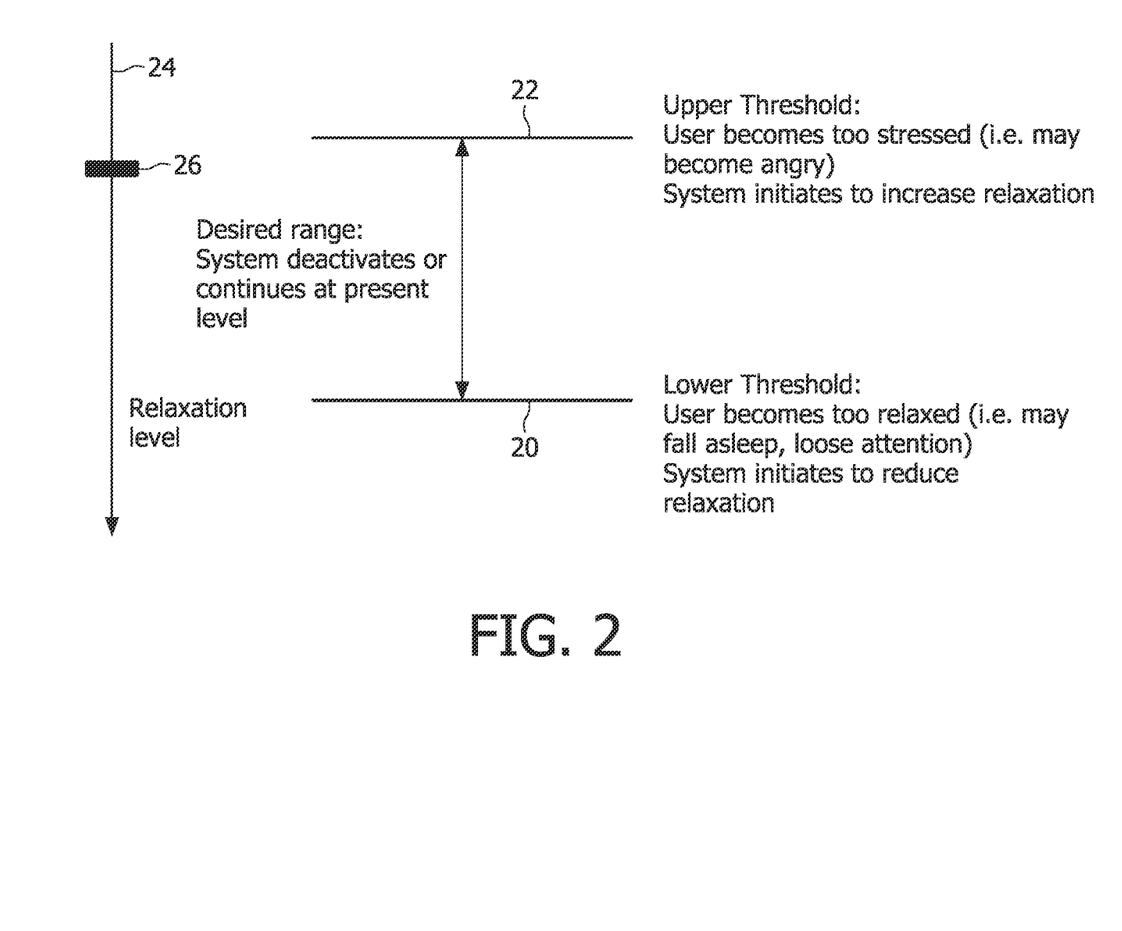
FIG. 2 is a schematic indication of the operation of the system of FIG. 1 with two threshold levels.

FIG. 2 shows a schematic indication of the operation of the system 10 according to one embodiment of this invention and illustrates how the system 10 interacts with the subject 12 depending upon the affective state (i.e. the level of the emotions) of the subject 12. In this particular example the affective state is presented in terms of the relaxation state of a user 12 whilst in a driving situation. A lower threshold 20 represents the lower limit that the subject 12 is allowed to reach before an output is provided to the subject 12. In this case the lower threshold 20 represents the subject 12 becoming too relaxed perhaps approaching falling asleep while they are driving. An upper threshold 22 represents the maximum alertness that the subject 12 is permitted before; again, the system 10 will intervene to attempt to calm the subject 12. In the case of the upper threshold 22 the subject is perceived to be too stressed or angry once this limit is crossed to drive their vehicle in a safe manner. The scale 24 (which can be thought of as a relaxation scale) represents the perceived range of possible relaxation states of the subject 12 and the value 26 shows the current level that the subject 12 is calculated to have reached. This value 26 is calculated by the processor 16 using the data from the sensors 14.

The output provided to the subject 12 could take many different forms and could be a combination of different stimuli, both direct and indirect. FIG. 1 shows the possible use of a loudspeaker. In a further embodiment described below there is considered a system which helps to control the relaxation level of the car driver 12 using a breathing guidance system. The output that the user receives may be an adaptation of an already existing output. In this case the level of the output is changed when either threshold is exceeded. For example if the user is listening to audio then the output that they receive when the system ascertains that a threshold has been crossed will be a change in volume of the audio.

Breathing guidance is a method to improve someone's breathing techniques. Breathing influences heart rate (HR)

and hence heart-rate variability (HRV). HRV has become a topic of major interest in physiology and psychology. It is of particular interest because HRV is attributed to the balance between the parasympathetic (PNS) and the sympathetic (SNS) nervous system respectively decreasing and increasing the heart rate. As a consequence HRV is a measure of the relaxation level of the user, the more "coherent" the HRV (i.e. the more smoothly the HRV oscillates with time) the more relaxed the user.

The connection between being relaxed via meditation and breathing is shown in studies on the impact of meditation on cardio respiratory synchronization with respect to breathing oscillations and the modulations of heart rate induced by respiration (respiratory sinus arrhythmia, RSA), see for example Dirk Cysarz, Arndt Bussing, "Cardio respiratory synchronization during Zen meditation", European Journal of Applied Physiology, 95(1), pages. 88 to 95, 2005. Zen meditation synchronizes the cardio respiratory interaction with respect to breathing oscillations and the heart rate variations induced by respiration (RSA). Furthermore, it drastically increases low-frequency variations of heart rate. Spontaneous breathing patterns hardly showed any cardio respiratory synchronization and during mental activity the cardio respiratory synchronization was decreased compared to both types of Zen meditation. Furthermore, the above paper indicates that this kind of religious practice has immediate physiological effects on cardio respiratory interaction without the need of special long-term training. For yoga similar results are obtained, as shown by E. Jovanov, "On Spectral Analysis of Heart Rate Variability during Very Slow Yogic Breathing", 27th Annual International Conference of the Engineering in Medicine and Biology Society, IEEE-EMBS 2005, pages 2467 to 2470, 2005.

In order to guide the breathing, either, firstly a stimulus is given which the user follows (i.e. breath in at the moment of the first signal, breath out at the second). The simplest method of achieving this is simply to provide a slow, repetitive signal as is provided by the RESPeRATE® device. A more powerful approach is to tune the breathing guiding signal to another body signal for example Voluntary cardiorespiratory synchronization (VCRS) can be initiated. VCRS is a method to synchronize breathing to the heart rate (HR) and thereby to obtain a certain heart-rate variability (HRV). As the system will in any case be monitoring the affective state of the user, it may be possible to use the monitoring device to pace the VCRS, providing that the monitoring device is able to derive a heart rate. Secondly, the subject can be encouraged to breath freely but feedback is provided to the subject as to how coherent their HRV is—this is the approach taken by the StressEaser device, and also by Heart Math and Wild Divine.

The system of the present invention is, in an exemplary embodiment based around a car or other vehicle. The system described contains three blocks, measuring (sensing), controlling, and feedback. The first step is the breathing guidance sensing in this exemplary embodiment based upon heart rate sensing which can be determined in a variety of ways which include:

With classical electrical Ag/Ag Cl electrodes measuring the ECG signal

Measuring the ballistocardiogram, for example with a static charge sensitive bed (SCSB), or a piezo foil, or an EMFi-film sensor build into a chair, see for example, Junnila, S.; Akhbardeh, A.; Varri, A.; Koivistoinen, T., "An EMFi-film sensor based ballistocardiographic chair performance and cycle extraction method", IEEE Workshop on Signal Processing Systems Design and Implementation, 2005. Volume, Issue 2 to 4, pages 373 to 377, November 2005.

Measuring the oxygen saturation (SPO2)

Measuring the (photo-)plethysmogram PPG, in the finger, ear, or somewhere else on the body of the subject Using non-galvanic capacitive electrodes (see C. J. Harland, T. D. Clark and R. J. Prance, "High resolution ambulatory electrocardiographic monitoring using wrist-mounted electric potential sensors", Meas. Sci. Technol. 14 (2003), pages 923 to 928.)

Using a wristwatch like device, see Monitoring apparatus for monitoring a user's heart rate and/or heart rate variation; wristwatch comprising such a monitoring apparatus, published as WO 2007/072288

Using seismosomnography (SSG) (see Brink et al., "Contact-free measurement of heart rate, respiration rate, and body movements during sleep", Behavior Research methods, 38(3), pages 511 to 521, 2006.)

Ultra Wide Band radar

Optical Vibrocardiography (see U. Morbiducci et al., "Optical Vibrocardiography: A novel tool for the Optical Monitoring of cardiac activity", Annals of biomedical engineering, Vol. 35(1), pages 45 to 58, January 2007.

Acoustical with a microphone (phonocardiogram)

Intelligent textile or underwear with build in sensors

Alternative embodiments could make use of direct breathing rate detection using for example strain gauges built into chest straps or underwear or alternatively using acoustic techniques or the ballisto cardiogram approach described above. The advantage of measuring the heart rate is that it provides the option to incorporate the VCRS methods described in detail below to guide the breathing of the subject (as well as monitoring the coherence in the HRV as a possible feedback mechanism to the driver).

In still further embodiments (not necessarily related to the driving situation) other physiological signals which are related to other affective states could be considered. For example analysis of speech (for application in customer facing environments such as call centers) could be used to determine the level of stress of the user, whilst the measurement of facial expression or facial movement (eye blinking, eye tracking etc.) could be used to assess the level of attention of the user.

Whilst any of the above measurements could be considered in the case of the driver a preferred embodiment is integration of the measurement of the subject's physiological parameters into the driver cockpit area. Here, the following options could be considered:

Integration of the sensor into the seat belt. This is particularly preferred as the seat belt is positioned across the chest area and in intimate contact with the body—a combination which facilitates reliable measurement of e.g. heart rate or breathing.

Integration of the sensor into the seat e.g. ballisto cardiogram e.g. with an EMFi-film sensor built into the driver seat Integration of the sensor into the steering wheel (as the driver is usually holding the wheel)

Use of a camera to monitor the facial expression/movement of the driver, (relatively easy as driver is in a fixed position).

Use of a microphone to monitor breathing (relatively easy as driver is in a fixed position—allows e.g. good noise cancellation possibilities). Here a preferred embodiment would build this into a "hands free" set.

Preferably this measurement is unobtrusive and the preferred sensing method depends on the application. Once the ECG or a similar signal is known, the time between the R peaks (primary heartbeat signals) can be determined yielding the inter beat intervals (IBI).

The second step is the feedback controller in this exemplary embodiment based upon the VCRS approach. The feedback controller operates to maintain the affective state of the user within the pre-defined region, as shown in FIG. 2. In the case of the driver, when driving a vehicle the driver can be more relaxed if he is breathing in a VCRS way. If it appears that the driver relaxes too much and may fall in sleep the system can operate such that the driver gets more aroused by being encouraged to increase their breathing rate. Alternatively, if the system notes that the driver is becoming too stressed it can slow down the breathing rate to increase relaxation.

In the following, some details of the VCRS approach are given. Before 1964, the only method to control the respiratory induced variation whilst studying the patients' heart was for the subject or patient to hold his breath. In 1964 the first known solution to the respiratory variations in the electrocardiogram/vector cardiogram (ECG/VCG) was in a paper Schmitt published on techniques for signal averaging (see for example R. B. Patterson, A. Belalcazar, and Pu Yachuan, "Voluntary cardio-respiratory synchronization", IEEE Engineering in Medicine and Biology Magazine, 23(6), pages 52 to 56, November/December 2004). In this paper subjects were signaled using a light or sound to breathe synchronized at a sub multiple of their heart rate. The signal was created from the ECG by counting for example two beats for the inspiration signal and the next three beats for the expiration signal. Each of the beats or RR time intervals with the same position in the respiratory cycle (i.e. first, second, third, etc.) were computer averaged to eliminate noise and other variations that occur unsynchronized with the heart beat, see FIGS. 3 and 4. This resulted in a very noise-free signal representing respiratory sinus arrhythmia (RSA) changes in the beat-to-beat heart rate or RR interval. The non respiration variations are reduced as the square root of number of breath cycles.

Figure 3:
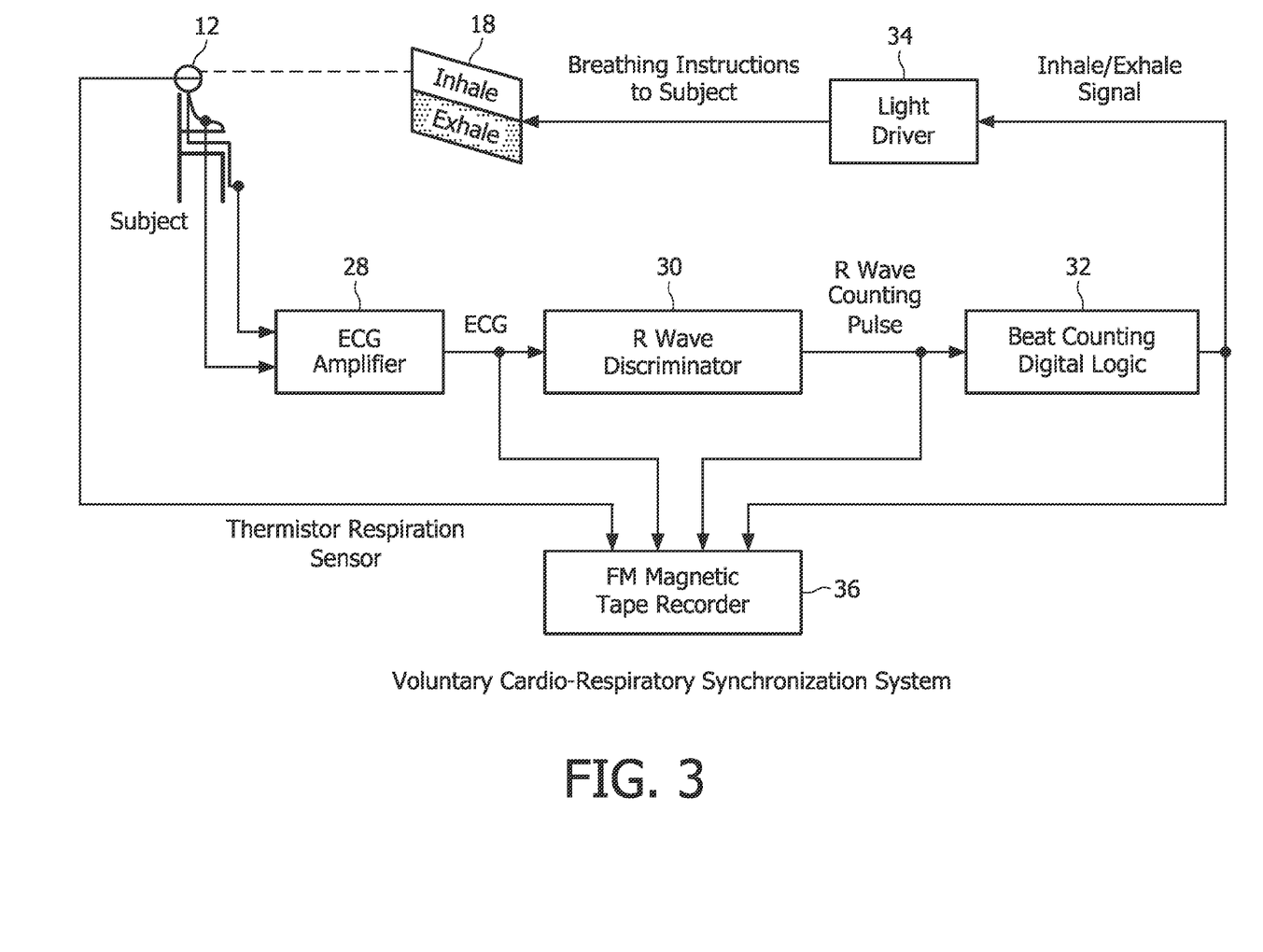
FIG. 3 is a schematic diagram of a voluntary cardiorespiratory synchronization system.

FIG. 3 shows an example of a voluntary cardio-respiratory synchronization (VCRS) scheme which can be used to support a breathing level in a subject 12, in order to regulate the heart rate of the subject 12. The system of FIG. 3 can be used to maintain the heart rate (or the interpreted relaxation level) of the subject 12 within the upper and lower thresholds, as desired. The subject 12 is monitored and has the physiological parameters associated with their heart measured by sensors, the output of which is received at an ECG amplifier 28.

The amplified ECG signal is passed to an R wave discriminator 30 which outputs an R wave counting pulse to a beat counting logic circuit 32. This logic controls a light driver 34 which controls an output device 18 which is comprised of lights that illustrate to the subject 12 when the subject should inhale and exhale. The system shown in FIG. 2 need not be intrusive for the subject 12 for example if they are wearing a small wrist-mounted device that monitors their heart rate. The relaxation level of the subject 12 is detected, and when the level crosses either of the lower or upper thresholds, then output is provided to the subject 12 via the lights 18. While the subject 12 is monitored by the system, then data can recorded at the recorder 36.

Figure 4:
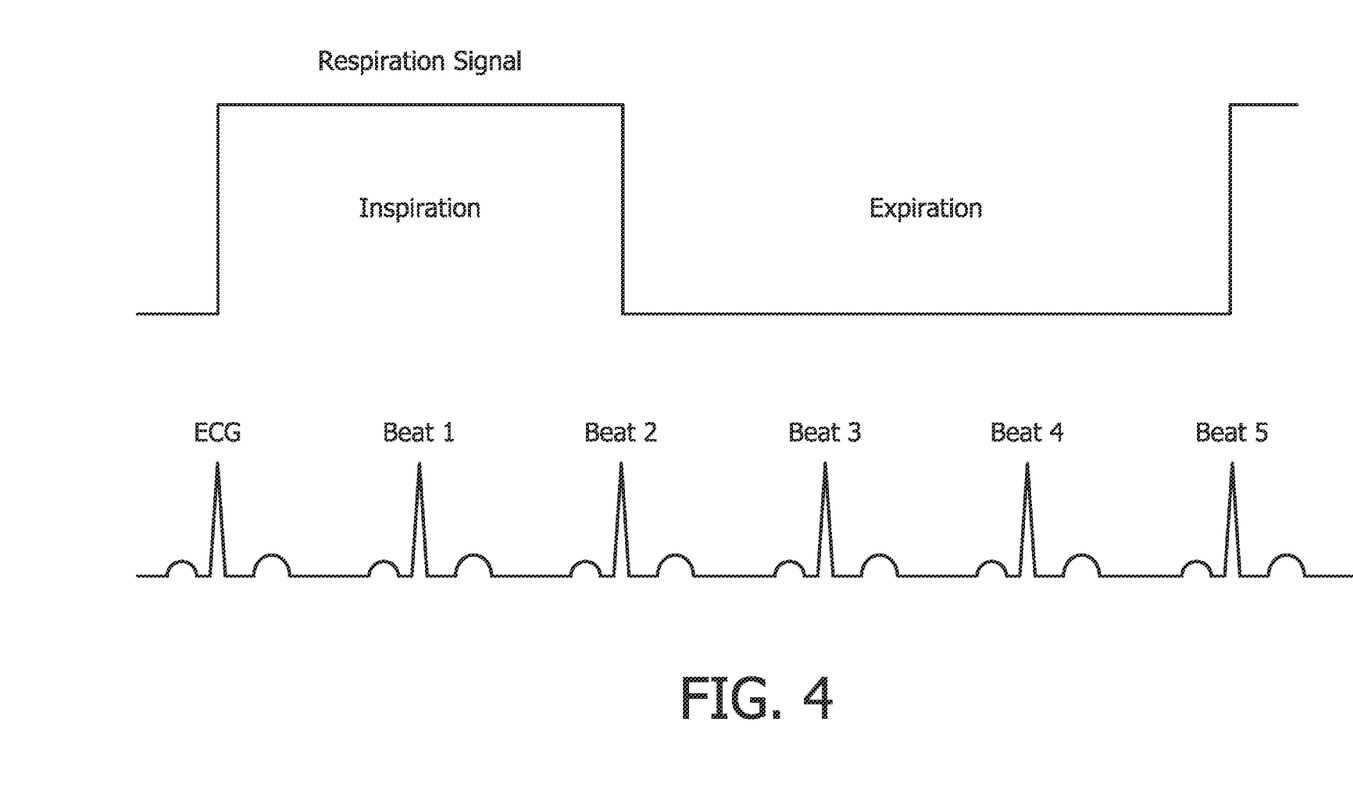
FIG. 4 is a timing diagram.

FIG. 4 shows a VCRS timing diagram, with the output of the R wave discriminator 30 shown in the lower portion of the Fig., and the generation of a respiration signal at the top of the Fig. This respiration signal is used to control the lights 18 which signal to the subject 12 the information that the subject 12 needs in order to control their breathing. The scheme of FIGS. 3 and 4 is one way in which an output can be provided to a subject 12 in order to control the relaxation level of the subject 12. If it is calculated that the user is becoming too relaxed and their relaxation level has been calculated to be below the lower threshold on the scale then the lights 18 can be controlled to speed up the breathing of the subject 12. In the opposite sense if the subject 12 is considered to be too stressed and their measured relaxation level is above the upper threshold then the lights 18 can be used to slow down the breathing of the subject 12.

Figure 5:
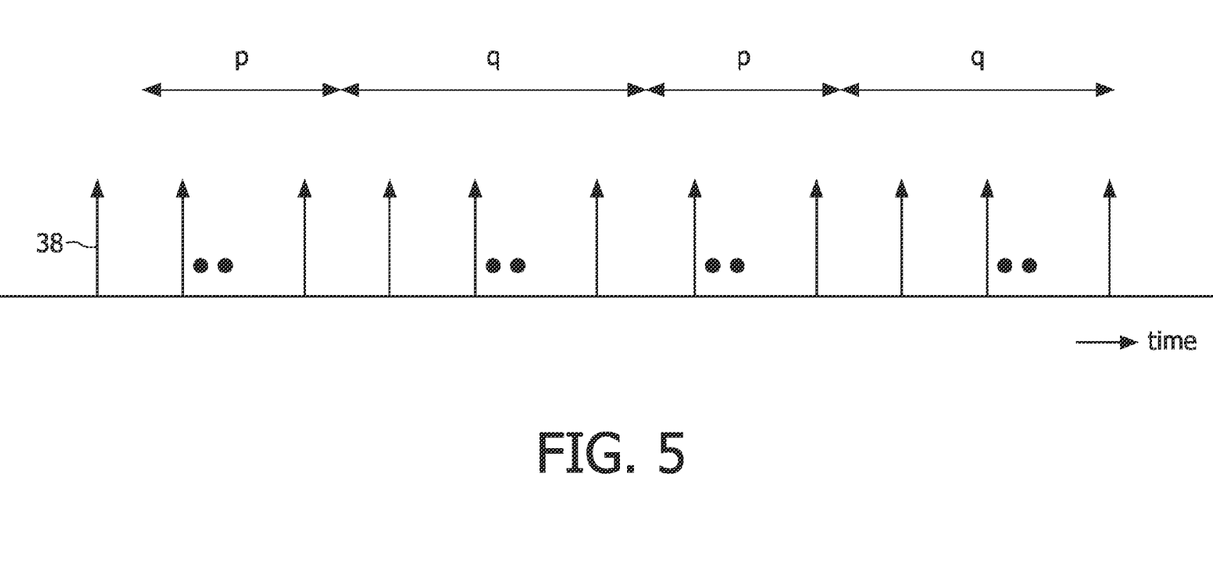
FIG. 5 is a further timing diagram.

The calculation of when to make the outputs to the subject 12 is shown in FIG. 5. It is possible to assign intervals with real numbers p and q such that during the p interval or at the transition from q to p there is a 'breath in' control signal and at the transition from p to q there is a 'breath out' control signal. In the Fig., each arrow 38 illustrates a heartbeat. Between the p and q intervals there are int(p) and int(q) heartbeats respectively where 'int' denotes the integer operation. Heart beat is here considered in a wide sense; it can be derived directly from the ECG, but also from acoustics or from the PPG. The values of p and q are not restricted to integers such as in traditional VCRS. This gives more freedom to the user, it gives even more freedom than prior art systems which dictate int(p)=int(q). These values p and q may be chosen individually or even adapted to the subject, since this depends on the subject's tidal volume and cardiac output. The system 10 can even give feedback to the user 12 if the breathing is done properly as dictated by monitoring the respiration using PPG, or other means.

The transients between p and q and vice versa are not necessarily coincident with a heart beat. This gives important freedom; furthermore it makes more sense from a physiological point of view. In particular if the beat 'arrows' 38 are derived from a finger PPG then there is a significant delay between the relevant pulse in the ECG and the PPG. The only restriction is that the intervals p and q vary proportional to the corresponding heart beat activity time axis, hence remaining phase locked. In the simplest embodiment p and q are integers and coinciding with the measured pulse (the arrows 38 in FIG. 5). The arrows 38 indicate a heartbeat but the transients between intervals p and q and vice versa are not necessarily coincident with a heart beat.

In a refined embodiment the positions of the 'arrows' 38 are predicted with an Auto Regressive (AR) filter, so that in cases that the measured signal is unreliable, the AR function predict their correct position (including the variation) which is much more refined than filling in previous values, or the average value. It is also possible to use an adaptive schema to determine initial values for p and q by letting the subject 12 breath in and out at their own pace and determining the breathing pace via the ECG-output, for example with a piezo foil, or from the PPG. Hence it is possible to easily determine initial values for p and q. Typical values could be p=2, q=3, but as a starting value the system 10 can use values for p and q that the subject 12 is currently using, and increase those numbers gradually.

In another embodiment, the system 10 can be configured to not necessarily demand that the breathings are exact in synchronization with the respiration, but it suffices to be almost in synchronization. From the theory of weakly coupled chaotic systems it is known that if $$|n\Phi_H - m\Phi_R| < \epsilon$$

where n and m are integers, $\Phi_H$ and $\Phi_R$ are the phases of the heart and respiratory signals respectively, and E is a sufficiently small constant number the signals can be considered as being phase locked.

The third step carried out by the system 10 is the applying of the feedback to the subject 12. In the embodiment above, this is based upon breathing guidance, and may be triggered by any of the human senses, for example, by sound, scent, touch, or a light which may change in color or brightness. Some embodiments and applications are listed below.

If the feedback is given by means of headphones, the system 10 can modify for example by volume one headphone, say the left one, as an indication of inhale, and the other as exhale. An alternative to this can be using a voice with a relaxing intonation, for example saying breath in and breath out.

The signal is sent wirelessly to a LivingColor lamp, so the color wheel of the LivingColor lamp is steered by the feedback controller.

A movie/animation is displayed on a television screen, e.g. the sea with a beach and a flying seagull where as the wings go up the subject must breathe in and as the wings go down the subject must breathe out. An extension of the animation can be that there are more people together each having their own sensing control and feedback system. for example their own bird waving with the wings; the birds may be of different type, color, size, etc. A particular type of synchronization can be that all subjects try to wave the wings unison.

Another feedback modality is transcutaneous electrical nerve stimulation (TENS) which might be modulated by the feedback controller If a subject 12 is lying on bed the system 10 can be used as a fall-a-sleep aid the cardio signals and optionally also the breathing rate signals are measured by one of the methods described but preferably with a ballisto cardiogram, so that the subject 12 is free to move. The feedback can be given by modulating lights at a modest level but also a relaxing humming sound at modest sound level which might be modulated by the feedback controller, or a (synthetic) music sound or a vibrating element (e.g. in pillow) or a heating element (e.g. in pillow or bed sheet) can be used. In this fall-a-sleep aid by analysis of the cardio signals or the breathing rate signals the system can determine whether the person is approaching the sleep state and adjust the feedback (for instance advised breathing frequency or signal intensity) in order to optimize a sleep coaching process. Furthermore, the system can determine whether the subject has actually been fallen asleep. That is if the cardio signals for instance are below a certain threshold then it will be highly probable that the subject has fallen asleep. And if so, the volume or intensity of the feedback is reduced for example in a gradual manner such that the subject does not wake up from the change in feedback. Furthermore, if the measured cardio signals indicate a state of restless sleep or almost waking up then the system can decide to increase or change the feedback in such a way that the subject is coached into a better sleep state or a more convenient waking up experience.

During sports activities for example gym, running, and rowing, the sportsman can get feedback in particular runners often wear already a HR measurement device for example a polar strap. In some activities a device is touched, such as the steering wheel of a bike where easily the ECG can be measured many other gym apparatuses have such contacts.

In hospitals patients are often already hooked up to SPO2-clips or EEG electrodes so that the feedback controller can 'tap' these signals easily and send them to the feedback device. Similarly in hospitals patients while being operated during partial anesthesia can breathe voluntarily. They are hooked up to SPO2-clips or EEG electrodes so that the feedback controller can 'tap' these signals easily and send them to the feedback controller and by applying VCRS the operation will be less stressful. If the subject gets mechanical ventilation, for example after surgery the system 10 can dictate the ventilation pace of the ventilation machine such that it gets synchronized with the subject's heart rate in this case it is not voluntary respiration but it is synchronized.

Instead of the two phase aid with feedback to inhale and exhale the system can be extended to multiple phases. Similar feedback techniques as mentioned above can be used but the simplest embodiment is to use four (colored) LED's pointing to a text or just a variable text which phase is ongoing. For example, a particular form of yoga known as Nadi Shodhana Pranayama or alternate nostril breathing encompasses four breathing phases: inhalation, internal retention (keeping lungs full), exhalation, and external retention (keeping lungs empty). The duration of breathing phases is controlled by mental counting in the ratio of 1:2:2:1, and in general p, q, r, and t, similar to the p and q discussed above. Inhalation and exhalation take place through alternating the active nostril, keeping the other nostril closed. Traditionally, the right nostril is closed by the thumb and left nostril is closed with the ring finger. For example, during the first cycle the practitioner would inhale through the left nostril, keeping right nostril closed, than keep the breath in ("internal retention") with both nostrils closed, exhale through right nostril only, and finally close both nostrils during external retention. The next cycle starts by inhaling through the right nostril. The practice consists of ten cycles of slow breathing.

Finally, it is possible to synchronize the subject's heartbeats and the respiration with a locomotion frequency, such as the steps during walking or running, or the movements during rowing, etc.

Figure 6:
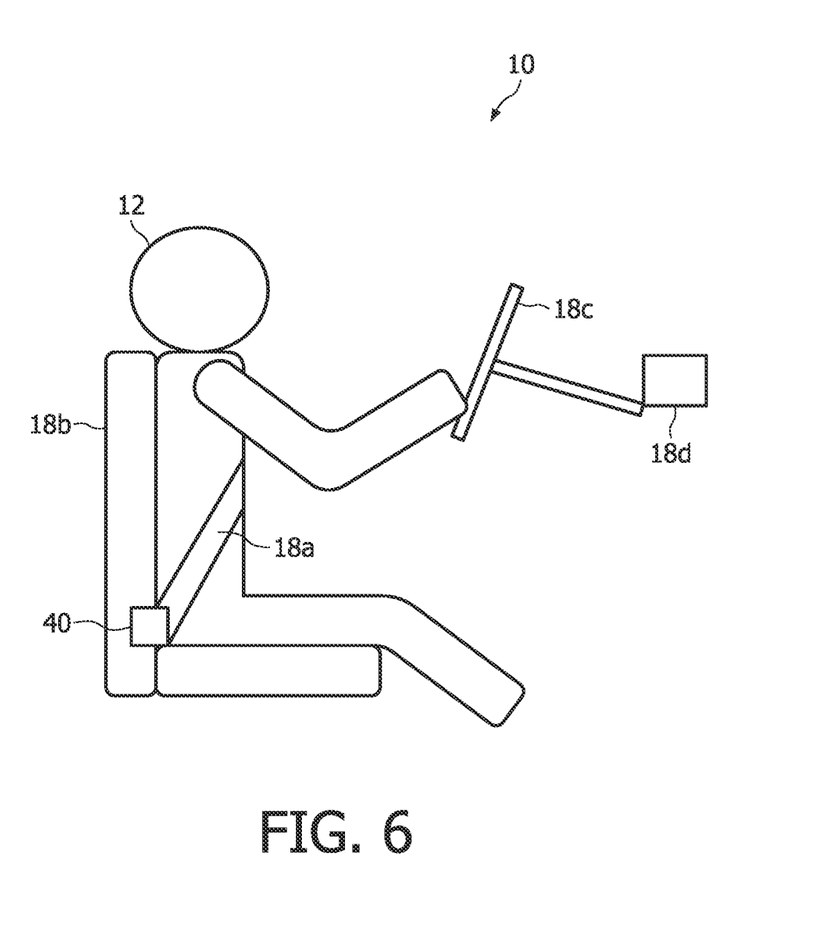
FIG. 6 is a second embodiment of the system of FIG. 1.

Whilst any of the above methods of applying feedback could be considered, in the case of the driver a preferred embodiment may be integration of the feedback into the driver cockpit area. FIG. 6 shows an example of such a system 10, focused on the feedback elements 18. The sensors and processing components are not shown, but can be in any suitable form as discussed above, for example relative to FIG. 1. Here the following options could be considered to provide breathing guidance:

Integration of the feedback into a seat belt 18a. As the seat belt 18a is positioned across the chest area of the subject 12 and is in intimate contact with the subject's body it would be natural to induce a breathing rate by for example either repeatedly tightening and slackening the belt slightly with a tightening device 40 or applying a regular tactile stimulus (such as a short vibration) or using a heat pulse.

Integration of the feedback into a seat 18b. This will allow this output device 18b to apply a regular tactile stimulus (such as a short vibration) or using a heat pulse via the driver seat. Similarly integration of the feedback to the subject 12 can be via a steering wheel 18c (as the driver is usually holding the wheel) by applying a regular tactile stimulus (such as a short vibration) or using a heat pulse for example.

Other possibilities include the use of an audio system in the vehicle to generate the feedback as an audio cue, and the use of an air conditioning system 18*d* could be used to generate repeated cues to promote guided breathing (such as producing repeated gusts of air, repeated scent releases etc.). In addition several other car related feedback methods could be applied in order to, for example, stop a driver from relaxing too much, for example changing the car temperature providing an invigorating scent, increasing air flow, and/or choosing a "power song" from the subject's music collection.

When driving a vehicle the driver can be more relaxed if he is breathing in a VCRS way in the vehicle chair 18*b* there can be easily built in a heart rate detector for example via an EMFi-film sensor based ballistocardiographic chair (as detailed in Junnila, S.; Akhbardeh, A.; Varri, A.; Koivistoinen, T. "An EMFi-film sensor based ballistocardiographic chair performance and cycle extraction method", IEEE Workshop on Signal Processing Systems Design and Implementation, 2005. Volume, Issue 2-4, pp. 373-377, November 2005). If it appears that the driver relaxes too much and may fall in sleep, the system 10 can operate such that the driver gets more aroused by increasing the breathing rate. Alternatively, if the system 10 notes that the driver is becoming too stressed it can slow down the breathing rate to increase relaxation.

The system 10 is applicable in many other situations in general situations where people are interacting not just with machinery but also with other people (when driving, at work, aircraft pilots, train drivers, shop assistants or counter workers (banks, local council), call centre personnel), where it is important to not only stay alert (i.e. limit the amount of relaxation) but also to avoid becoming too stressed or too aroused, as this will also limit peoples ability to function optimally.

For this reason this invention provides systems and methods to assist users to remain in a region of affective state (e.g. relaxation or arousal) defined by both a lower threshold and an upper threshold. Whilst the examples in this document have been presented in terms of the relaxation state of a user whilst in a driving situation, it is clear that the invention can be advantageously applied in many other situations (as listed above) and for many other affective stares (such as fear, anger, surprise, boredom, disgust, happiness etc.).

The invention claimed is:

1. A method of maintaining an affective state in a subject including a desired breathing rate comprising the acts of:
    measuring at least one physiological parameter of the subject by an at least one sensor;
    calculating by a processor, using the at least one measured physiological parameter, a value representing a relaxation state of the subject;
    determining by the processor if the calculated value is below a lower threshold or above an upper threshold, wherein the lower threshold represents a lower limit that the subject is allowed to reach and at which the subject becomes too relaxed and wherein the upper threshold represents a maximum alertness that the subject is permitted and at which the subject becomes too aroused;
    generating at least one output by an output device to the subject comprising generating a first output for reducing relaxation if the calculated value is determined to be below the lower threshold and generating a second output for increasing relaxation if the calculated value is determined to be above the upper threshold, the second output being different from the first output; and
    mapping two measured physiological parameters of the at least one measured physiological parameter of the subject to a scale including the lower threshold and the upper threshold; and
    placing a single indication of the calculated value on the scale, wherein the single indication on the scale of the relaxation state of the subject is based on measurements from a first sensor and a second sensor of the at least one sensor which are configured to measure the two measured physiological parameters which are different from each other and indicates that the subject is more stressed than relaxed when the single indication is closer to the upper threshold than to the lower threshold and that the subject is more relaxed than stressed when the single indication is closer to the lower threshold than to the upper threshold,
    wherein a first physiological parameter of the at least one measured physiological parameter is used to determine the upper threshold of the scale and a second physiological parameter of the at least one measured physiological parameter is used to determine the lower threshold of the scale, the first physiological parameter being provided from the first sensor of the at least one sensor and the second physiological parameter being provided from the second sensor of the at least one sensor, the first sensor being different from the second sensor,
    wherein the first physiological parameter is different from the second physiological parameter.

2. The method according to claim 1, wherein the generated output comprises direct physical feedback to the subject.

3. The method according to claim 1, wherein the relaxation state is controlled by breathing guidance.

4. The method of claim 1, wherein the first sensor is configured to determine a heart rate of the subject for determining the upper threshold of the scale and the second sensor is configured to determine one of a head movement and facial expression of the subject for determining the lower threshold of the scale.

5. The method of claim 1, wherein the first physiological parameter comprises a heart rate of the subject and the second physiological parameter comprises one of a head movement and facial expression of the subject.

6. A system for maintaining an affective state in a subject including a desired breathing rate comprising:
    at least one sensor configured to measure at least one physiological parameter of the subject;
    a processor configured to calculate, using the at least one measured physiological parameter, a value representing a relaxation state of the subject, and to determine if the calculated value is below a lower threshold or above an upper threshold, wherein the lower threshold represents a lower limit that the subject is allowed to reach and at which the subject becomes too relaxed and wherein the upper threshold represents a maximum alertness that the subject is permitted and at which the subject becomes too aroused; and
    at least one output device configured to generate at least one output to the subject, wherein the at least one output device is further configured to generate a first output for reducing relaxation if the calculated value is determined to be below the lower threshold and to generate a second output for increasing relaxation if the calculated value is determined to be above the upper threshold, the second output being different from the first output, wherein the processor is further configured to map two measured physiological parameters of the at least one measured physiological parameter of the subject to a scale including the lower threshold and the upper threshold, and place a single indication of the calculated value on the scale, wherein the single indication on the scale of the relaxation state of the subject is based on measurements from a first sensor and a second sensor of the at least one sensor which are configured to measure the two measured physiological parameters which are different from each other and indicates that the subject is more stressed than relaxed when the single indication is closer to the upper threshold than to the lower threshold and that the subject is more relaxed than stressed when the single indication is closer to the lower threshold than to the upper threshold, wherein a first physiological parameter of the at least one measured physiological parameter is used to determine the upper threshold of the scale and a second physiological parameter of the at least one measured physiological parameter is used to determine the lower threshold of the scale, the first physiological parameter being provided from the first sensor of the at least one sensor and the second physiological parameter being provided from the second sensor of the at least one sensor, wherein the first sensor is different from the second sensor, and wherein the first physiological parameter is different from the second physiological parameter.

7. The system according to claim 6, wherein the at least one output device is arranged to provide direct physical feedback to the subject.

8. The system according to claim 7, wherein the at least one output device further comprises a portion of a seat for the subject.

9. The system according to claim 7, wherein the at least one output device further comprises a portion of a steering wheel for the subject.

10. The system according to claim 8, wherein the at least one output device further comprises a vibrator configured to output a vibration.

11. The system according to claim 8, wherein the at least one output device further comprises a heater configured to output a heat pulse.

12. The system according to claim 7, wherein the at least one output device further comprises an air conditioning system and a control device arranged to control the air conditioning system.

13. The system according to claim 6, wherein the relaxation state is controlled by using a breathing guidance system.

14. The system of claim 6, wherein the first sensor is configured to determine a heart rate of the subject for determining the upper threshold of the scale and the second sensor is configured to determine one of a head movement and facial expression of the subject for determining the lower threshold of the scale.

15. The system of claim 6, wherein the first physiological parameter comprises a heart rate of the subject and the second physiological parameter comprises one of a head movement and facial expression of the subject.

16. A computer-readable storage-medium that is not a transitory propagating signal or wave, the medium modified by control information including instructions for performing a method of maintaining an affective state in a subject including a desired breathing rate comprising the acts of:

measuring at least one physiological parameter of the subject by an at least one sensor;

calculating by a processor, using the at least one measured physiological parameter, a value representing a relaxation state of the subject;

determining by the processor if the calculated value is below a lower threshold or above an upper threshold, wherein the lower threshold represents a lower limit that the subject is allowed to reach and at which the subject becomes too relaxed and wherein the upper threshold represents a maximum alertness that the subject is permitted and at which the subject becomes too aroused;

generating at least one output by an output device to the subject comprising generating a first output for reducing relaxation if the calculated value is determined to be below the lower threshold and generating a second output for increasing relaxation if the calculated value is determined to be above the upper threshold, the second output being different from the first output; and mapping two measured physiological parameters of the at least one measured physiological parameter of the subject to a scale including the lower threshold and the upper threshold; and placing a single indication of the calculated value on the scale, wherein the single indication on the scale of the relaxation state of the subject is based on measurements from a first sensor and a second sensor of the at least one sensor which are configured to measure the two measured physiological parameters which are different from each other and indicates that the subject is more stressed than relaxed when the single indication is closer to the upper threshold than to the lower threshold and that the subject is more relaxed than stressed when the single indication is closer to the lower threshold than to the upper threshold, wherein a first physiological parameter of the at least one measured physiological parameter is used to determine the upper threshold of the scale and a second physiological parameter of the at least one measured physiological parameter is used to determine the lower threshold of the scale, the first physiological parameter being provided from the first sensor of the at least one sensor and the second physiological parameter being provided from the second sensor of the at least one sensor, the first sensor being different from the second sensor, wherein the first physiological parameter is different from the second physiological parameter.

* * * * *